(12) United States Patent
Richter et al.

(10) Patent No.: US 6,887,265 B2
(45) Date of Patent: May 3, 2005

(54) BALLOON EXPANDABLE COVERED STENTS

(75) Inventors: Jacob Richter, Ramat Hasharon (IL); Joseph Flomenblit, Holon (IL); Natalia Budigina, Holon (IL)

(73) Assignee: Medinol Ltd., Tel-Aviv (IL)

(*) Notice: Subject to any disclaimer, the term of this patent is extended or adjusted under 35 U.S.C. 154(b) by 0 days.

(21) Appl. No.: 10/234,701

(22) Filed: Sep. 3, 2002

(65) Prior Publication Data

US 2003/0036792 A1 Feb. 20, 2003

Related U.S. Application Data

(63) Continuation of application No. 09/178,571, filed on Oct. 26, 1998, now Pat. No. 6,475,234.

(51) Int. Cl.$^7$ .................................................. A61F 2/06
(52) U.S. Cl. ........................................ 623/1.15; 623/909
(58) Field of Search ............................ 623/1.11–1.16, 623/1.34, 1.46

(56) References Cited

U.S. PATENT DOCUMENTS

| | | | |
|---|---|---|---|
| 3,620,212 A | | 11/1971 | Fannon et al. |
| 4,425,908 A | | 1/1984 | Simon |
| 4,494,531 A | | 1/1985 | Gianturco |
| 4,776,337 A | | 10/1988 | Palmaz |
| 4,795,458 A | | 1/1989 | Regan |
| 5,147,370 A | | 9/1992 | McNamara et al. |
| 5,207,706 A | | 5/1993 | Menaker |
| 5,246,445 A | | 9/1993 | Yachia et al. |
| 5,282,823 A | | 2/1994 | Schwartz et al. |
| 5,330,500 A | * | 7/1994 | Song ................... 623/1.2 |
| 5,383,927 A | | 1/1995 | De Goicoechea et al. |
| 5,443,496 A | * | 8/1995 | Schwartz et al. .......... 623/1.16 |
| 5,464,419 A | | 11/1995 | Glastra |
| 5,464,438 A | | 11/1995 | Menaker |
| 5,522,882 A | | 6/1996 | Gaterud et al. |
| 5,536,274 A | | 7/1996 | Neuss |

(Continued)

FOREIGN PATENT DOCUMENTS

| | | |
|---|---|---|
| EP | 0 709 068 | 5/1996 |
| EP | 0732089 | 9/1996 |
| EP | 0819412 | 1/1998 |
| EP | 0836839 | 4/1998 |
| EP | 839506 | 5/1998 |
| EP | 895761 | 2/1999 |
| JP | 2102669 | 4/1990 |
| JP | 8-141090 | 6/1996 |
| JP | 8-229136 | 10/1996 |
| JP | 8-336597 | 12/1996 |
| JP | 10-80492 | 3/1998 |
| WO | 95/31945 | 11/1995 |
| WO | 97/21403 | 6/1997 |
| WO | WO 98/05720 | 2/1998 |
| WO | 98/12989 | 4/1998 |
| WO | 98/27894 | 7/1998 |
| WO | 98/38947 | 9/1998 |
| WO | 99/65419 | 12/1999 |

*Primary Examiner*—David H. Willse
*Assistant Examiner*—Suzette J-J. Gherbi
(74) *Attorney, Agent, or Firm*—Kenyon & Kenyon

(57) ABSTRACT

The present invention provides stents for deploying within tubular organs, blood vessels, or other tubular body lumens. Such stents comprise a stent body comprising an elastic material, the stent body being characterized by a free cylindrical shape having a free diameter. The stent body is at least partially covered with a covering that substantially prevents the stent body from expanding towards its free diameter when the stent body is placed into a diameter smaller than the free diameter. In one embodiment, the covering is a metal coating on the stent body. In another embodiment, the covering is a tube, or multiple tubes, around the stent body. Also provided is a method for deploying the stents of the present invention within tubular organs, blood vessels, or other tubular body lumens.

11 Claims, 4 Drawing Sheets

U.S. PATENT DOCUMENTS

| | | | |
|---|---|---|---|
| 5,607,442 A | * 3/1997 | Fischell et al. | 623/1.18 |
| 5,607,467 A | 3/1997 | Froix | |
| 5,628,786 A | 5/1997 | Banas et al. | |
| 5,628,787 A | 5/1997 | Mayer | |
| 5,628,790 A | 5/1997 | Davidson et al. | |
| 5,700,285 A | * 12/1997 | Myers et al. | 623/1.13 |
| 5,713,949 A | 2/1998 | Jayaraman | |
| 5,725,572 A | 3/1998 | Lam et al. | |
| 5,779,732 A | 7/1998 | Amundson | |
| 5,814,063 A | 9/1998 | Freitag | |
| 5,824,045 A | 10/1998 | Alt | |
| 5,824,046 A | * 10/1998 | Smith et al. | 623/1.13 |
| 5,843,164 A | 12/1998 | Frantzen et al. | |
| 5,855,600 A | * 1/1999 | Alt | 623/1.15 |
| 5,873,904 A | * 2/1999 | Ragheb et al. | 623/1.13 |
| 5,922,020 A | 7/1999 | Klein et al. | |
| 5,922,393 A | 7/1999 | Jayaraman | |
| 5,964,771 A | * 10/1999 | Beyar et al. | 606/108 |
| 6,086,610 A | * 7/2000 | Duerig et al. | 623/1.18 |
| 6,174,329 B1 | 1/2001 | Callol et al. | |
| 6,241,757 B1 | 6/2001 | An et al. | |

* cited by examiner

BALLOON EXPANDABLE COVERED STENTS

RELATED PATENT APPLICATIONS

This application is a continuation of U.S. patent application Ser. No. 09/178,571 filed on Oct. 26, 1998 now U.S. Pat. No. 6,475,234.

FIELD OF THE INVENTION

The present invention relates to implantable medical devices and to covered implantable stents comprising an elastic or superelastic material.

BACKGROUND OF THE INVENTION

Stents are support structures that are implanted in tubular organs, blood vessels or other tubular body lumens to help keep such conduits open. Stents are often used following balloon angioplasty to prevent restenosis and may, more generally, be used in repairing any of a number of other tubular body lumens, such as those in the vascular, biliary, genitourinary, gastrointestinal, respiratory and other systems.

The materials used in fabricating stents must be chemically and biologically inert to living tissue. Stents must further be able to stay in position and continue to support the tubular body lumens into which they are implanted over extended periods of time. Moreover, stents must have the ability to expand from a contracted state, which facilitates insertion into a body lumen, to an expanded diameter that is useful in supporting at least a portion of the body lumen. This expansion is accomplished either mechanically, such as by the action of a balloon-ended catheter, or by self-expansion such as by shape-memory effects or by the use of a constrained elastic stent.

The above requirements limit the number of eligible stent materials. One of the most widely used metal alloy systems is the nickel-titanium system, the alloys of which are known as nitinol. Under certain conditions, nitinol is highly elastic such that it is able to undergo extensive deformation and yet return to its original shape. Elastic stents are typically deployed in a body lumen by reducing the diameter of the stent by mechanical means, restraining the stent in the reduced diameter during insertion into the body, and releasing the stent from the restraint at a target location. Once released, the stent "self-expands" to its predetermined, useful diameter by virtue of its elastic properties. One of the advantages of elastic stents is that, after deployment, they are able to "rebound" to their useful diameters after being deformed by external forces. The resilient nature of such stents not only make them ideal for self-expansion upon delivery to a target location, but it also makes them desirable for use in body lumens that are often subjected to external forces and corresponding temporary reductions in diameter or other deformations. For example, elastic stents are useful for placement in the carotid artery, which is frequently deformed by external forces because the vessel is in close proximity to the body surface.

There are, however, some potential drawbacks associated with conventional elastic stents. For example, such self-expanding stents possess a single predetermined diameter, thus limiting the use of a given stent and increasing the number of different stents required to cover a range of useful diameters. Where the predetermined diameter is larger than the body lumen in which the stent is placed, residual expansion forces often result in the gradual, undesired expansion of the surrounding lumen. The release of self-expanding stents often does not exert sufficient force to open blocked body lumens containing hard plaque. It is thus sometimes necessary to perform the additional step of inserting a balloon into the partially-deployed stent for further dilation, thus adding cost, time and risk to the overall procedure.

SUMMARY OF THE INVENTION

The present invention provides stents for deploying within tubular organs, blood vessels, or other tubular body lumens. Such stents comprise a stent body comprising an elastic material, the stent body being characterized by a free cylindrical shape having a free diameter. The stent body is at least partially covered with a covering that substantially prevents the stent body from expanding towards its free diameter when the stent body is placed into a diameter smaller than the free diameter. In addition, after the stent is expanded, the covering does not force the stent body to a diameter smaller than the diameter to which it is expanded. In one embodiment, the covering is a metal coating on the stent body. In another embodiment, the covering is a tube around the stent body. In yet another embodiment, the covering includes multiple rings around the stent body.

The present invention also provides methods for deploying the stents of the present invention within tubular organs, blood vessels, or other tubular body lumens. The method includes the steps of providing a stent comprising a stent body comprising an elastic material, the stent body being characterized by a free cylindrical shape having a free diameter; deforming the stent to a diameter smaller than the free diameter; covering the stent with a covering that substantially prevents the stent body from expanding towards the free diameter when the stent body is placed into a diameter smaller than the free diameter; inserting the stent into the body while in the reduced diameter; and mechanically expanding the stent. In one embodiment, the step of covering the stent comprises the step of coating the stent body. In another embodiment, the step of covering the stent comprises the step of placing a tube over the stent. In yet another embodiment, the step of covering the stent comprises the step of placing multiple rings over the stent.

One advantage of the present invention is that it provides stents that are isothermally deployed in the body.

Another advantage of the present invention is that it provides stents that resist loads exerted by a surrounding tubular organ.

Another advantage of the present invention is that it provides expanded stents that are reboundable and resilient along their longitudinal and radial axes, and thus resist deformation when exposed to longitudinal and radial forces.

Yet another advantage of the present invention is that it provides stents that are expanded to controlled, desired dimensions by balloon catheters, and each stent can be expanded to any diameter within a wide range of diameters.

DETAILED DESCRIPTION

The present invention exploits the advantages of conventional elastic stents while minimizing the potential limitations and drawbacks of such stents. For example, the stents of the present invention are not limited to predetermined "learned" diameters and do not require post-placement dilation procedures separate from the deployment stage. Moreover, the stents of the present invention are each expandable to a range of useful diameters. Furthermore, when expanded to useful diameters at target locations within body lumens, the stents of the present invention are resilient such that they rebound to their expanded diameters after being subjected to external forces that result in temporary reductions in diameter or other deformations.

Generally, the stents of the present invention comprise a stent body comprising an elastic material, and a covering on the stent body. The covering substantially prevents the stent body from expanding towards its free diameter when the stent body is placed into some smaller diameter. A stent of the present invention is deployed within a body lumen by deforming the stent to a diameter smaller than its free diameter, covering the stent with a covering that substantially prevents the stent from expanding towards its free diameter by virtue of its elastic properties, inserting the stent into the body lumen, and mechanically expanding the stent such as by balloon inflation to a desired, useful diameter at a target location within the body lumen.

Figure 1A:
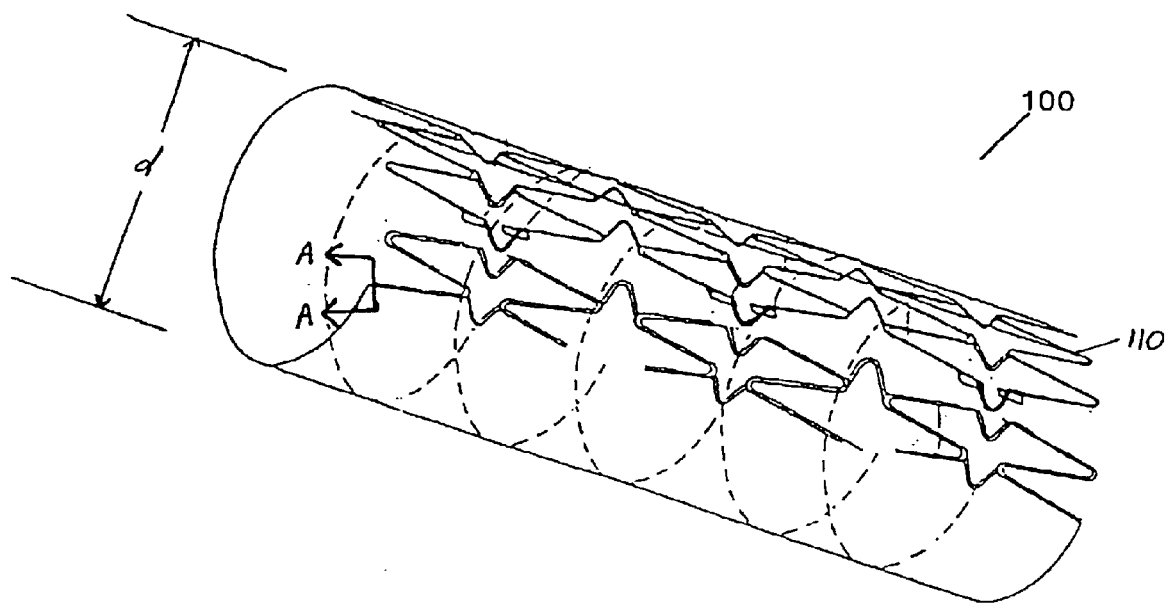
FIGS. 1A and 1B show planar and cross-sectional views, respectively, of an embodiment of the present invention in which a stent is covered with a metal coating.

In accordance with an embodiment of the invention as shown in FIG. 1A, a stent 100 has a stent body 110 having a free cylindrical shape of free diameter, d. The cylindrical shape and diameter, d, of the stent body 110 are said to be "free" when the stent body 110 is not acted upon by external forces. Although the stent 100 is in the form of a patterned tube, other suitable stent configurations (for example, wire coil, braids, hexagons, nets, spiral ribbons, zig-zags, articulated stents, and the like) are also within the scope of the present invention.

The stent body 110 comprises an elastic material that is able to undergo appreciable recoverable (elastic) deformation upon the application of external forces without incurring extensive permanent (plastic) deformation. For example, the elastic material is preferably characterized by recoverable strains greater than about 1%, more preferably greater than about 5%. The elastic material is, for example, a metallic or polymeric material. The elastic material includes so-called "superelastic" materials such as certain nitinol alloys, which are typically characterized by recoverable strains greater than about 8%. Nitinol is a preferred material for the stent body 110.

Because the stent body 110 comprises an elastic material, it tends to spring back to its free configuration and free diameter after being deformed or compressed by external forces. However, the stent 100 includes a covering on the stent body 110 that substantially prevents the stent body 110 from expanding towards its free diameter when it is placed into a diameter smaller than its free diameter. Moreover, the covering holds the stent body 110 to the diameter to which it is expanded once positioned in a target location in the body. Therefore, in accordance with the present invention, it is not required that the useful diameter to which the stent may be expanded be substantially equal to the free diameter of the stent body 110.

In one embodiment, the covering on the stent body 110 is a coating 102 that preferably comprises a plastically deformable metal. The coating 102 optionally comprises an x-ray absorbing material, thus rendering the stent 100 radiopaque. Preferred materials for the coating 102 include gold, platinum, palladium and tantalum.

The coating 102 is applied to the stent body 110 by any suitable method such as, for example, dipping, spraying, vapor deposition, chemical or electrochemical plating, sputtering and the like. A preferred method for applying the coating 102 to the stent body 110 is by electroplating. The coating 102 is applied to a thickness, t(102), on the underlying stent body 110, the struts of which are characterized by a thickness, t(101), as shown in the cross-sectional view illustrated in FIG. 1B. The stent body 110 is either partially or completely covered with the coating 102. When the diameter of the stent 100 is reduced such as by crimping onto a balloon catheter, the thickness of the coating 102, t(102), is sufficient to provide the strength necessary to hold the stent body 110 at the reduced diameter, thus negating any tendency of the stent body 110 to expand to its free diameter, d, by virtue of its elastic properties. For example, when the coating 102 comprises a soft, pliable metal such as gold, and the stent body 110 comprises nitinol, the thickness of the coating 102 preferably approximates the cross-sectional thickness of the stent body struts. Conversely, when the coating 102 comprises a stronger metal, its thickness need not be as thick as the underlying stent body struts.

The coating 102 imparts desired properties to the stent 100. For example, when the coated stent 100 is expanded within the body, its compression resistance is a combination of the strength of the stent body 110 and the strength of the coating material, which is plastically deformed during expansion of the stent 100. The radial resistance of the stent 100 against stent collapse and recoil after deployment is thus greatly enhanced by the coating 102. When expanded, the coated stents of the present invention have the further advantage of being resilient in the longitudinal and radial directions, thereby resisting permanent deformation by longitudinal and radial forces. Furthermore, because the addition of the coating 102 to the stent 100 substantially prevents the stent body 110 from expanding towards its free diameter, it is not necessary to restrain the stent from expanding such as by sheath or other restraining means during insertion into the body.

Figure 1B:
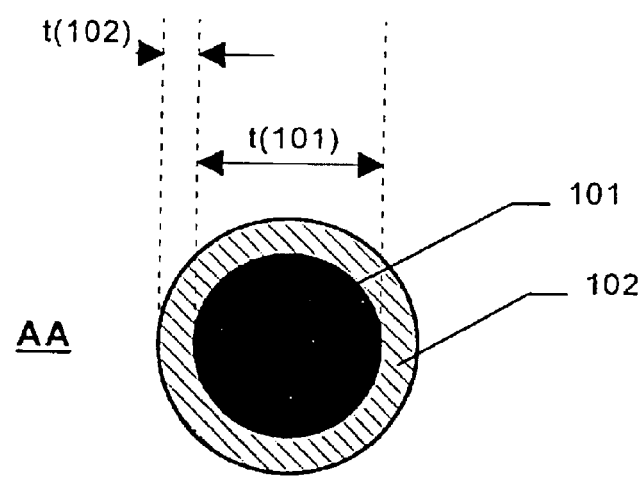
Figure 2:
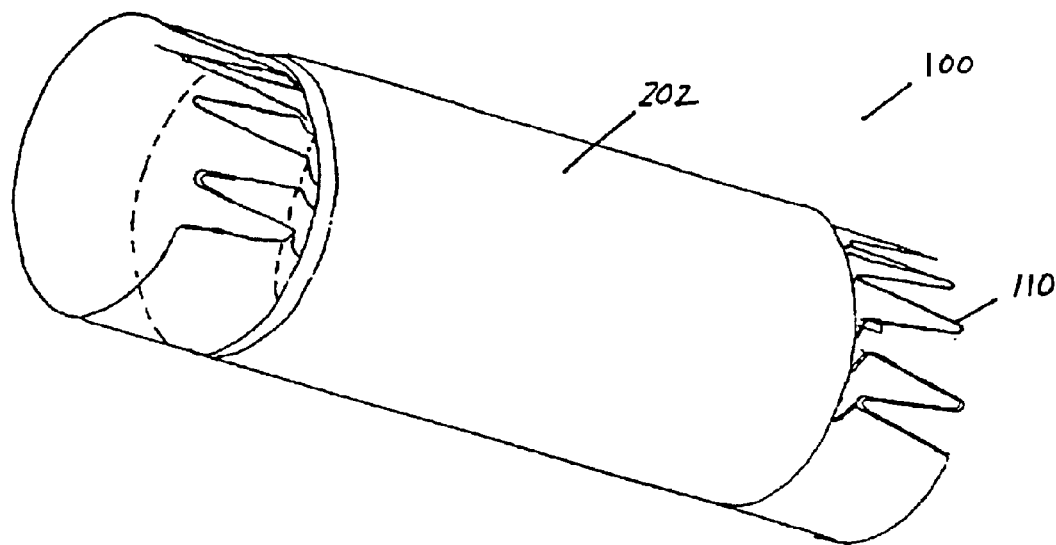
FIG. 2 shows an embodiment of the present invention in which a stent is covered with a tube.

FIG. 2 shows another embodiment of the present invention in which the stent 100 comprises a stent body 110 covered with a tube 202 rather than the coating 102 of the embodiment shown in FIG. 1B. The tube 202 comprises any suitable biocompatible material having sufficient strength to substantially prevent the stent body 110 from expanding towards its free diameter after the stent body 110 is placed into a diameter smaller than the free diameter. A preferred material for the tube 202 is implant-grade medical polyurethane. In the embodiment shown in FIG. 2, the length of the tube 202 is substantially the length of the stent 100. The thickness of the tube 202 is sufficient to provide the strength necessary to hold the stent body 110 at the reduced diameter, thus negating any tendency of the stent body 110 to expand to its free diameter, d, by virtue of its elastic properties. For example, when the stent body 110 comprises nitinol and the tube 202 comprises implant-grade medical polyurethane, the tube 202 is approximately 100 to 200 microns in thickness.

The tube 202 has potentially multiple functions. For example, the tube 202 prevents the stent body 110 from expanding to its free diameter after the stent body 110 is placed into a diameter smaller than the free diameter. Furthermore, because the length of the tube 202 is substantially the length of the stent body 110, it serves to limit embolization and growth through the openings between the struts of the stent 100. As another example, the tube 202 is optionally used for holding drug agents during delivery to a target location, whereupon the drug agents are released from the tube 202. For example, the tube 202 has drug agents embedded therein, which are subsequently released from the tube 202 at the target location to prevent or limit neo-intimal proliferation.

Figure 3:
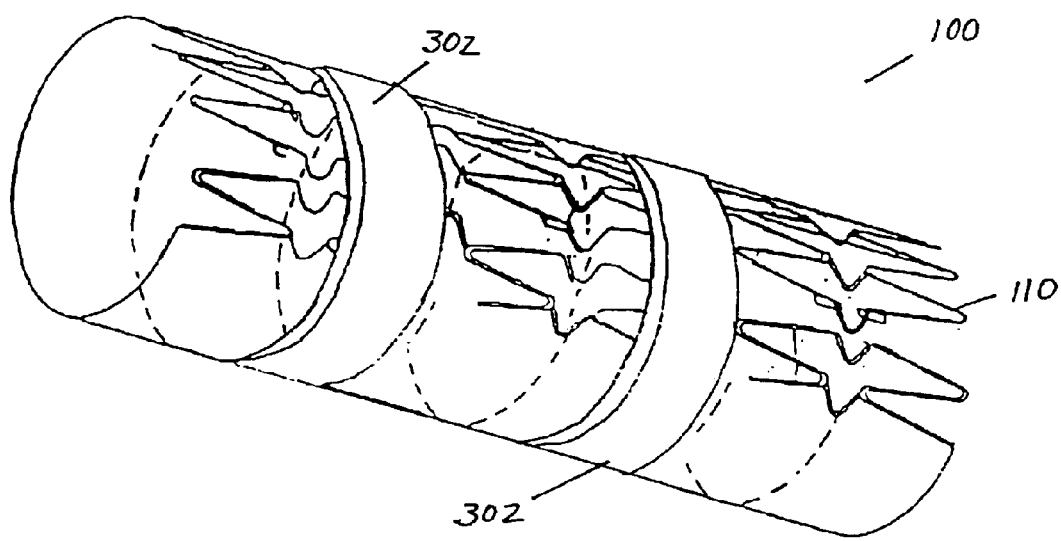
FIG. 3 shows an embodiment of the present invention in which multiple rings are situated around a stent.

Another embodiment of the present invention is shown in FIG. 3. This embodiment is similar to that shown in FIG. 2 with the exception that the embodiment shown in FIG. 3 includes multiple tubes or rings 302, each having a length less than that of the stent body 110. This embodiment is preferred over the embodiment shown in FIG. 2 in applications where the use of minimally covered stents are desired.

The present invention provides methods for deploying the stent 100 within a body lumen. In one embodiment, the method includes the steps of providing a stent comprising a stent body comprising an elastic material, the stent body being characterized by a free cylindrical shape having a free diameter; deforming the stent body to a diameter smaller than its free diameter; covering the stent with a covering that substantially prevents the stent body from expanding towards said free diameter by virtue of its elastic properties; inserting the stent into the body; and mechanically expanding the stent at a target location within the body lumen to a desired, useful diameter. The covering substantially prevents the stent from expanding during insertion into the body and placement to a target location within a body lumen. Moreover, after the stent is deployed, the covering holds the stent to the diameter to which it is expanded. Therefore, a stent of the present invention is expandable to a wide range of diameters, and it is not required that the useful diameter to which the stent is expanded be substantially equal to the free diameter of the stent body.

Figure 4A:
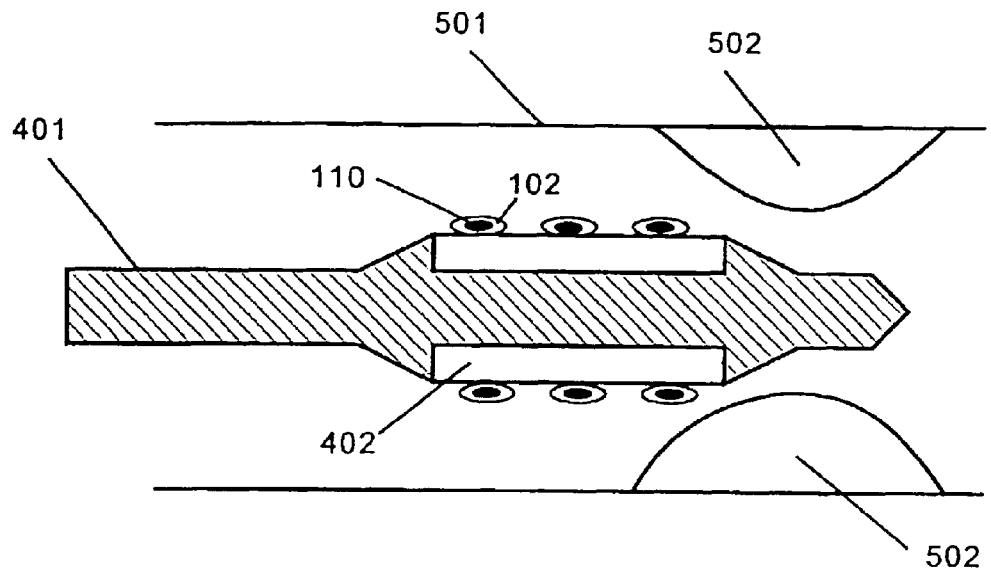
FIGS. 4A to 4C show a cross-sectional view of a method for deploying a stent into a body lumen, in accordance with the present invention.
Figure 4B:
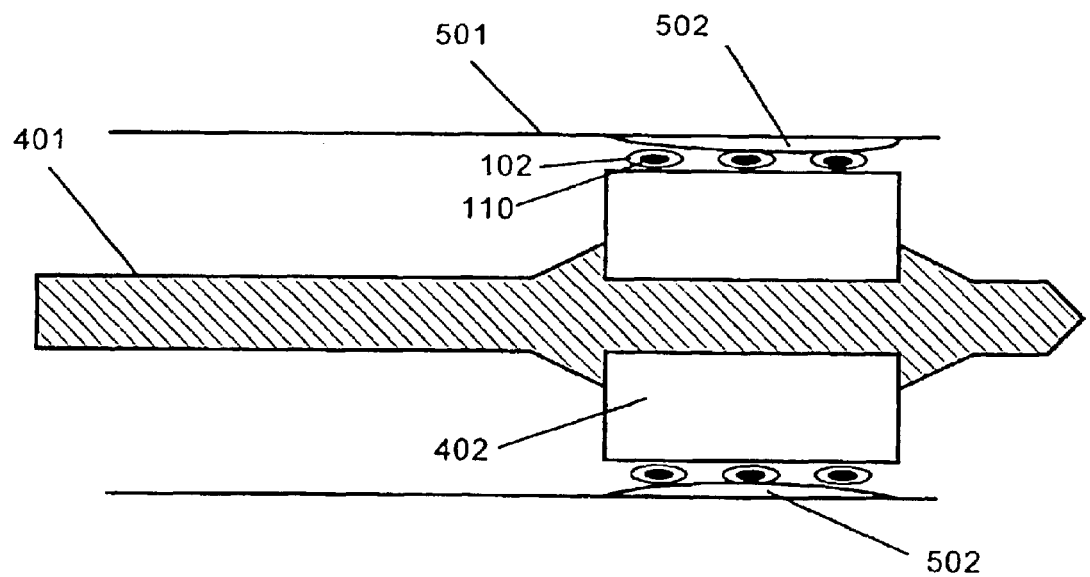
Figure 4C:
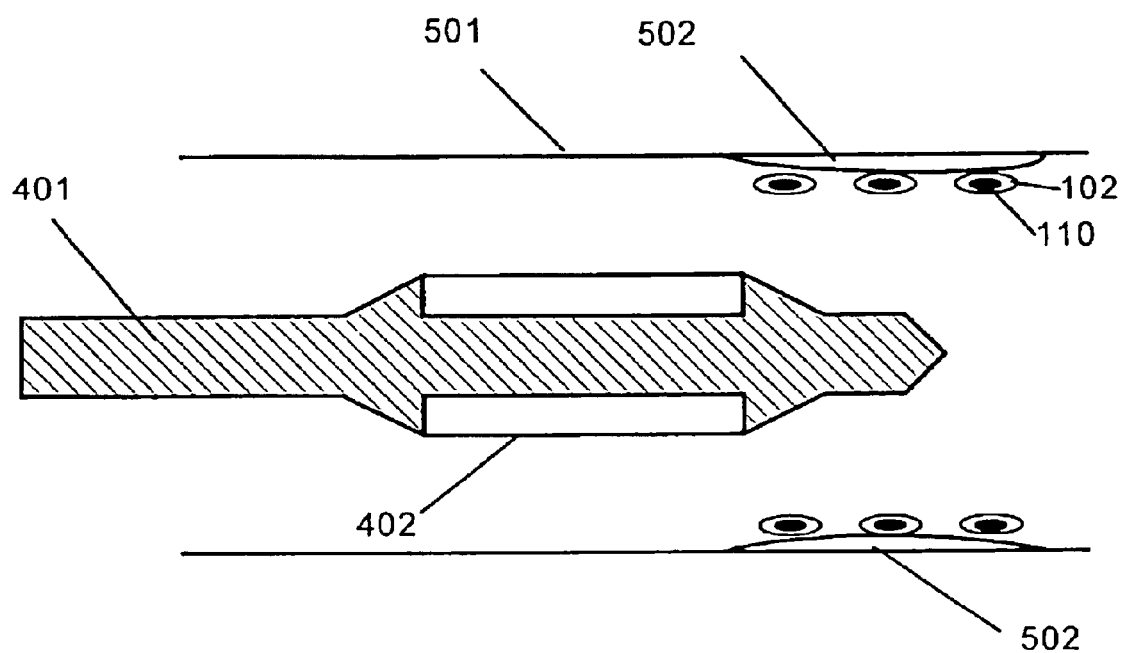

A method of deploying a stent is described with reference to FIGS. 4A to 4C, which illustrate (in cross-section) the deployment of a stent in an angioplasty procedure as a non-limiting example of the present invention. As shown in FIG. 4A, a stent having a stent body 110 and coating 102 on the stent body struts is mounted on a catheter 401 having an expandable portion 402. The diameter of the stent when mounted on the catheter 401 is less than its free diameter. Although the stent body 110 comprises an elastic material, the coating 102 is of sufficient strength to substantially prevent the stent body 110 from expanding towards its free diameter by virtue of its elastic properties. The catheter 401 is positioned within a body lumen 501 having a blockage caused by plague buildup 502, for example. When inserted to the desired target location, the expandable portion 402 of the catheter 401 is expanded by known techniques so to expand the stent to a desired, useful dimension as shown in FIG. 4B. During such expansion, the metal coating 102 on the stent body 110 undergoes plastic deformation. The expandable portion 402 of the catheter 401 is thereafter deflated to facilitate removal of the catheter 401 from the body lumen 501, as shown in FIG. 4C. The stent remains in place in an expanded configuration as shown in FIG. 4C.

The present invention is further described with reference to the following non-limiting examples.

EXAMPLE 1

Using known techniques, a patterned tube stent is made from nitinol having an approximate composition of 51 atomic percent nickel, balance titanium. The thickness of the stent struts is approximately 100 microns. The stent has a free diameter of about 5 millimeters. The stent is electroplated with gold using conventional techniques to a thickness of approximately 100 microns. The stent is thereafter deformed at room temperature, while the nitinol is in an austenitic phase, to a diameter of approximately 1 millimeter. The gold coating holds the stent to a diameter of approximately 1 millimeter.

The coated stent is crimped onto the expandable portion of a conventional balloon catheter. Using known techniques, the balloon catheter is delivered to a target location within a body lumen having a diameter of approximately 5 millimeters.

When the stent is positioned to the target location, the balloon catheter is expanded to a diameter of between about 3 to about 5 millimeters. During such expansion, the stent is likewise expanded to a diameter of between about 3 to about 5 millimeters and the gold layer is plastically deformed but remains as an intact coating. The balloon catheter is thereafter deflated and removed from the body, leaving the expanded stent in place at the target location. The deployed stent has high strength due to its austenitic phase and the additional strength imparted from the plastically deformed gold coating layer. In addition, the deployed stent has excellent resistance to recoil and collapse while maintaining resiliency in the longitudinal direction (i.e., reboundability).

EXAMPLE 2

Using known techniques, a patterned tube stent is made from nitinol having an approximate composition of 51 atomic percent nickel, balance titanium. The thickness of the stent struts is approximately 100 microns. The stent has a free diameter of about 5 millimeters.

The stent is cooled in ice water to place the nitinol in a martensitic phase and deformed while cold to a diameter of approximately 1 millimeter. A polyurethane tube, having a diameter of approximately 1.5 millimeters and a thickness of approximately 150 microns, is placed over the stent. Both the stent and the polyurethane tube have a length of about 1.5 centimeters. The polyurethane tube holds the stent to a diameter of approximately 1 millimeter.

The covered stent is crimped onto the expandable portion of a conventional balloon catheter. Using known techniques, the balloon catheter is delivered to a target location within a body lumen having a diameter of approximately 5 millimeters.

When the stent is positioned to the target location, the balloon catheter is expanded to a diameter of between about 3 to about 5 millimeters. During such expansion, both the stent and the polyurethane tube are likewise expanded to a diameter of between about 3 to about 5 millimeters. The balloon catheter is thereafter deflated and removed from the body, leaving the expanded stent and the polyurethane tube in place at the target location. The deployed stent has high strength due to its austenitic phase and the additional strength imparted from the plastically deformed gold coating layer. In addition, the deployed stent has excellent resistance to recoil and collapse while maintaining resiliency in the longitudinal direction (i.e., reboundability).

The present invention provides stents of improved strength that are isothermally deployed in the body without the need for restraining devices. When deployed in accordance with the present invention, the stents provide sufficient strength to resist recoil and collapse while maintaining resiliency in the longitudinal direction. It will be obvious to those skilled in the art, having regard to this disclosure, that other variations on this invention beyond those specifically exemplified here may be made. Such variations are, however, to be considered as coming within the scope of this invention as limited solely by the following claims.

We claim:

1. A method for deploying a stent within a body lumen, said method comprising the steps of:

providing a stent comprising a stent body comprising an elastic material, said stent body being characterized by a free cylindrical shape having a free diameter d;

deforming said stent body to a diameter smaller than said free diameter d;

covering said stent with a covering while said stent body is at said diameter smaller than said free diameter d, said covering substantially preventing said stent body from expanding towards said free diameter d and wherein said covering allows said stent body to be expanded to a useful diameter equal to or less than the free diameter d, and wherein after the expansion by a balloon catheter of said stent body once positioned in a target location of the body, to a useful diameter less than said free diameter d, said covering substantially prevents said expanded stent body from expanding towards said free diameter d;

inserting said stent into the body lumen; and mechanically expanding said stent.

2. The method of claim 1, wherein said step of covering said stent comprises the step of electroplating a metal coating onto said stent.

3. The method of claim 1, further comprising the step of mounting said stent onto a balloon catheter prior to the step of inserting said stent into the body.

4. The method of claim 3, wherein said step of mechanically expanding said stent comprises the step of inflating said balloon.

5. A method for deploying a stent within a body lumen, said method comprising the steps of:

providing a stent comprising a stent body comprising nitinol, said stent body being characterized by a free cylindrical shape having a free diameter d;

deforming said stent body to a diameter smaller than said free diameter d;

coating said stent with a metal coating while said stent body is at said diameter smaller than said free diameter d, said metal coating substantially preventing said stent body from expanding towards said free diameter d and wherein said metal coating allows said stent body to be expanded to a useful diameter equal to or less than the free diameter d, and wherein after the expansion by a balloon catheter of said stent body once positioned in a target location of the body, to a useful diameter less than said free diameter d, said metal coating substantially prevents said expanded stent body from expanding towards said free diameter d;

inserting said stent into the body lumen, with said nitinol in a substantially austenitic phase; and mechanically expanding said stent.

6. The method of claim 5, wherein, upon expansion of said stent body and said metal coating to a desired diameter, the metal coating does not force the stent body to a diameter smaller than that to which it is expanded.

7. The method of claim 5, wherein said step of coating said stent comprises the step of electroplating a metal coating onto said stent.

8. The method of claim 5, further comprising the step of mounting said stent onto a balloon catheter prior to the step of inserting said stent into the body.

9. The method of claim 8, wherein said step of mechanically expanding said stent comprises the step of inflating said balloon.

10. The method of claim 5, wherein said step of coating said stent comprises the step coating to a thickness approximately equal to the thickness of the stent body.

11. The method of claim 10, wherein said step of providing a stent comprises providing a stent with a stent body of a thickness of about 100 microns.

* * * * *